United States Patent [19]

Snyder, Jr. et al.

[11] 4,438,006
[45] Mar. 20, 1984

[54] PERFLUORINATED ALIPHATIC POLYALKYLETHER LUBRICANT WITH AN ADDITIVE COMPOSED OF AN AROMATIC PHOSPHINE SUBSTITUTED WITH PERFLUOROALKYLETHER GROUPS

[75] Inventors: Carl E. Snyder, Jr., Trotwood; Christ Tamborski, Dayton, both of Ohio

[73] Assignee: The United States of America as represented by the Secretary of the Air Force, Washington, D.C.

[21] Appl. No.: 418,113

[22] Filed: Sep. 14, 1982

[51] Int. Cl.$^3$ ............................................. C10M 1/10
[52] U.S. Cl. ................................. 252/49.9; 252/54; 252/389 A
[58] Field of Search ................... 252/49.9, 389 A, 54

[56] References Cited

U.S. PATENT DOCUMENTS

| | | | |
|---|---|---|---|
| 3,393,151 | 7/1968 | Dolle et al. | 252/49.9 |
| 3,481,872 | 12/1969 | Dolle et al. | 252/49.9 |
| 3,483,129 | 12/1969 | Dolle et al. | 252/49.9 |
| 3,499,041 | 3/1970 | Tamborski | 260/612 |
| 3,567,802 | 3/1971 | Garth | 260/950 |
| 3,665,041 | 5/1972 | Sianesi et al. | 260/615 A |
| 3,715,378 | 2/1973 | Sianesi et al. | |
| 3,847,978 | 11/1974 | Sianesi et al. | 260/535 H |
| 4,011,267 | 3/1977 | Tamborski et al. | 260/606.5 P |
| 4,043,926 | 8/1977 | Snyder et al. | 252/49.9 |
| 4,097,388 | 6/1978 | Snyder et al. | 252/49.9 |

*Primary Examiner*—Jacqueline V. Howard
*Attorney, Agent, or Firm*—Donald J. Singer; Charles E. Bricker

[57] ABSTRACT

A lubricant composition comprising a base fluid having the general formula

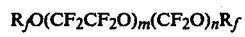

wherein $R_f$ is $CF_3$ or $C_2F_5$, m and n are integers whose sum is between 2 and 200, and the ratio of m to n is between 0.1 and 10, and a corrosion inhibiting amount of an aromatic phosphine with perfluorinated polyalkylether substituents having the general formula

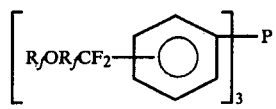

wherein $R_fOR_f$ is a perfluoroalkylether group containing at least one ether linkage.

10 Claims, No Drawings

PERFLUORINATED ALIPHATIC POLYALKYLETHER LUBRICANT WITH AN ADDITIVE COMPOSED OF AN AROMATIC PHOSPHINE SUBSTITUTED WITH PERFLUOROALKYLETHER GROUPS

RIGHTS OF THE GOVERNMENT

The invention described herein may be manufactured and used by or for the Government of the United States for all governmental purposes without the payment of any royalty.

BACKGROUND OF THE INVENTION

This invention relates to lubricating compositions.

Because of their thermal stability, perfluorinated polyalkylether fluids have great potential for use as engine oils, hydraulic fluids and greases. However, a serious drawback in their use results from the fact that certain metals, i.e., certain metals present in aircraft engine components, are corroded by these fluorinated fluids at elevated temperatures in an oxidative environment. For example, when the fluids are utilized as lubricants for mechanical components composed of mild steels, serious corrosion has occurred at temperatures of about 550° to 600° F. Stainless, steels, titanium and titanium alloys are attacked by the fluids at a temperature of about 600° F. Moreover, at elevated temperatures, particularly in an oxidizing atmosphere, the fluids themselves undergo considerable degradation, to the detriment of continued lubricating capacity.

An ideal lubricant composition would be one having a relatively constant viscosity such that it is flowable or pumpable over a wide temperature range, e.g., from about −50° F. to about 600° F. In general, base fluids available heretofore have either had a satisfactory viscosity at low temperatures, but degraded at elevated temperatures, or, were stable and had a satisfactory viscosity at elevated temperatures, but were too viscous to flow or pump at subzero temperatures. Consequently, it has been necessary to make compromises in the selection of base fluids dependent upon the use conditions to be encountered. Such compromises have not been entirely satisfactory.

In U.S. Pat. No. 3,393,151, issued to one of use as a coinventor of July 16, 1968, lubricants are disclosed that comprise a perfluorinated aliphatic polyether and a perfluorophenyl phosphorus compound. In U.S. Pat. No. 3,499,041, issued to one of us on Mar. 3, 1970, certain perfluoroaryl phosphines are disclosed as being anticorrosion additives for perfluorinated fluids. In U.S. Pat. No. 3,483,129, issued to one of us as a coinventor on Dec. 9, 1969, certain perfluorinated phenoxyphenyl phosphines are disclosed as being anticorrosion additives for perfluorinated fluids. In U.S. Pat. No. 3,567,802, certain perfluoropolyoxo alkane substituted phosphinates are disclosed as being useful as corrosion and degradation inhibitors for perfluorinated fluids. In U.S. Pat. No. 4,011,267, issued to us as coinventors on Mar. 8, 1977, certain fluorinated phosphines are disclosed as being anticorrosion and antioxidation additives for perfluorinated fluids. While the phosphorus compounds described in these patents exhibit corrosion inhibiting properties, at low temperatures they are generally only poorly soluble in perfluorinated fluids. Also, certain members of the classes of phosphorus compounds possess high volatility characteristics for long term high temperature applications. Because of these limitations, perfluorinated fluids containing such anticorrosion additives are not completely satisfactory for use in long term, wide temperature range applications.

It is an object of this invention to provide a lubricant composition which had little if any corrosive effect upon ferrous and titanium alloys.

Another object of this invention is to provide a lubricant composition which has a relatively constant viscosity over a wide temperature range.

Yet another object of this invention is to provide a lubricant composition which undergoes substantially no degradation when exposed to titanium.

Other objects and advantages of the invention will be apparent to those skilled in the art upon consideration of the following disclosure.

SUMMARY OF THE INVENTION

In accordance with the present invention there is provided a lubricant composition comprising (1) a base fluid consisting essentially of a mixture of linear fluorinated polyethers having the following formula:

$$R_fO(CF_2CF_2O)_m(CF_2O)_nR_f$$

wherein $R_f$ is $CF_3$ or $C_2F_5$, m and n are integers whose sum is between 2 and 200, and the ratio of m to n is between 0.1 and 10, and (2) a corrosion inhibiting amount of an aromatic phosphine with perfluorinated polyalkylether substituents having the general formula:

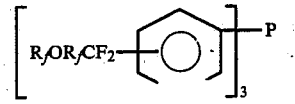

wherein $R_fOR_f$— is a perfluoroalkylether group containing at least one ether linkage. Examples of $R_fOR_f$— groups include the following:
$C_3F_7O[CF(CF_3)CF_2O]_xCF(CF_3)$—,
$C_2F_5O(CF_2CF_2O)_yCF_2$—, and
$CF_3O(CF_2O)_zCF_2$—, where x, y and z are zero or an integer having a value of 1 to 20, preferably 1 to 4, inclusive. A detailed description of the synthesis of these phosphine compounds is contained in application Ser. No. 418,115, filed of even date herewith by C. Tamborski, C. E. Snyder, Jr., and J. B. Christian, the disclosure of which is incorporated herein by reference. The preferred phosphines are those in which the perfluoroalkylether group is para to the phosphorus atom.

The $(CF_2CF_2O)_m$ and $(CF_2O)_n$ groups of the fluorinated polyether base fluids are randomly distributed in the polyether molecules. The integers m and n can also be defined as having values such that the fluorinated polyethers have a kinematic viscosity ranging from about 15 to about 1000 centistokes (cs) at 100° F. as determined by the method of ASTM D445. The fluorinated polyethers are normally obtained as mixtures of molecules, each of which has a well defined molecular weight. The usual practice is to fractionate the mixture so as to obtain a product having a desired average molecular weight or a desired kinematic viscosity. A more complete discussion of the base fluids may be found in U.S. Pat. No. 3,715,378, issued to D. Sianesi et al on Feb. 6, 1973. These fluorinated polyethers are available commercially from Montedison S.p.a., Milan, Italy, under the designation Fomblin Z, one particularly useful fraction of which has a viscosity of about 16 cs at 100° F.

In formulating the lubricant of this invention, a corrosion-inhibiting amount of the phosphine compound is mixed with the fluorinated polyether base fluid. The amount of the phosphine used generally ranges from 0.05 to 5 weight percent, preferably 0.5 to 2 weight percent, based upon the weight of the base fluid.

The following example illustrates the invention.

EXAMPLE

A series of runs was conducted for the purpose of determining the effectiveness of lubricant compositions of this invention. Lubricant compositions were formulated by mixing (1) a base fluid having the formula given previously, and having a kinematic viscosity of about 16 cs at 100° F., and (2) a fluorinated phosphine having the following formula:

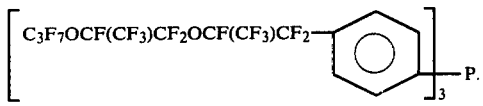

The base fluid used was Fomblin Z fluid, a product of Montedison S.p.a., Milan, Italy.

In the runs, specimens of steel, titanium and titanium alloys were immersed in the formulations that were prepared. The compositions of the steel and titanium alloys are described in the literature. For comparison purposes, runs were carried out in polyether fluid which did not contain the phosphine additive. The materials were contained in an oxidation test tube having a take-off adapter coupled to an air entry tube. An aluminum block both provided the means for heating the test tube and an "overboard" test procedure (no reflux condenser) was followed.

Air was bubbled through the materials at the rate of 1 liter of air per hour for a period of 24 hours. The runs were conducted at temperatures ranging from 500° to 600° F. The specimens and the apparatus were weighed before and after each run.

The data obtained in the runs are set forth below in the tables.

TABLE I

| Temperature (°F.) | 500 | 500 | 525 | 525 | 550 | 550 | 575 | 600 |
|---|---|---|---|---|---|---|---|---|
| Wt % Additive | 0 | 1.0 | 0 | 1.0 | 0 | 1.0 | 1.0 | 1.0 |
| Kinematic Viscosity Change at 100° F., % | −67 | +3.0 | −96.1 | +1.9 | −85.0 | −2.0 | +2.7 | +2.1 |
| Fluid Loss Wt % | 28 | 0 | 57.8 | 0.4 | 73.2 | 0.75 | 0.70 | 0.30 |
| Acid Number Increase mg KOH/g | 22.5 | 0.1 | 67.7 | 0.1 | 2.14 | 0.1 | 0.1 | 0.1 |
| Wt Change in mg/cm² | | | | | | | | |
| 4140 Steel | +0.22 | +0.14 | −0.19 | +0.74 | −1.12 | +0.01 | +0.02 | −0.04 |
| 52100 Bearing Steel | +0.04 | +0.05 | +0.30 | +0.46 | +0.50 | +0.06 | −0.04 | +0.35 |
| 410 Stainless Steel | −1.67 | −0.04 | −1.59 | +0.05 | −1.79 | +0.04 | −0.07 | +0.02 |
| M-50 Tool Steel | −0.27 | +0.04 | +0.08 | +0.24 | −1.12 | +0.05 | +0.09 | +3.55 |
| 440 C. Stainless Steel | −2.11 | +0.03 | −2.55 | +0.08 | −3.39 | +0.06 | −0.02 | +0.04 |

TABLE II

| Temperature (°F.) | 525 | 525 | 550 | 575 | 600 |
|---|---|---|---|---|---|
| Wt % Additive | None | 1.0 | 1.0 | 1.0 | 1.0 |
| Kinematic Viscosity Change at 100° F., % | −96.1 | +3.06 | +4.34 | +3.37 | +2.33 |
| Fluid Loss Wt % | 68.9 | 19.5 | 0.65 | 0.75 | 0.15 |
| Acid Number Increase mg KOH/g | 100.3 | 0.16 | 0.10 | 0.08 | 0.06 |
| Wt Change in mg/cm² | | | | | |
| Ti (6Al 4 V) | −0.09 | +0.07 | +0.01 | +0.02 | −0.09 |
| Ti (Pure) | −0.19 | +0.19 | +0.01 | +0.04 | +0.09 |
| Ti (4Al 4 Mn) | −0.13 | +0.12 | 0.00 | +0.03 | +0.13 |

The data in the foregoing tables show that the lubricant compositions of the invention have little, if any, corrosive effect upon titanium and ferrous and titanium alloys. Also, there was substantially no degradation of the lubricant compositions at the elevated temperatures even though the base fluid per se was severely degraded. Due to the nearly complete degradation and subsequent loss of the base fluid at 575° F. and 600° F. in the presence of ferrous alloys, and at 550°, 575° and 600° F. in the presence of titanium alloys, it was not possible to provide comparative data at those temperatures. Because of their outstanding properties, the lubricants of this invention can be employed for applications requiring extreme temperature conditions. Thus, the lubricants of this invention may be employed, for example, as gas turbine engine lubricants, nonflammable hydraulic fluids, greases compatible with liquid oxygen, liquid coolants and general purpose lubricants.

Various modifications may be made in the present invention without departing from the spirit of the invention or the scope of the following claims.

We claim:

1. A lubricant composition comprising (1) a base fluid consisting essentially of a mixture of linear fluorinated polyethers having the formula $$R_fO(CF_2CF_2O)_m(CF_2O)_nR_f$$

wherein $R_f$ is $CF_3$ or $C_2F_5$, m and n are integers whose sum is between 2 and 200 and the ratio of m to n is between 0.1 and 10; and (2) a corrosion inhibiting amount of an aromatic phosphine with perfluorinated polyalkylether substituents having the formula

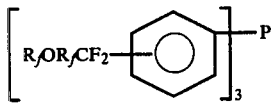

wherein $R_fOR_f$— is a perfluoroalkylether group containing at least one ether linkage.

2. The composition of claim 1 wherein the amount of said phosphine ranges from about 0.05 to 5 weight percent.

3. The composition of claim 1 wherein the amount of said phosphine ranges from about 0.5 to 2 weight percent.

4. The composition of claim 1 wherein said $R_fOR_f$— in said phosphine is

wherein x is zero or an integer having a value of 1 to 20.

5. The composition of claim 4 wherein said x is in the range of 1 to 4.

6. The composition of claim 4 wherein said x is 1.

7. The composition of claim 1 wherein said $R_fOR_f$— in said phosphine is

wherein y is zero or an integer having a value of 1 to 20.

8. The composition of claim 7 wherein said y is in the range of 1 to 4.

9. The composition of claim 1 wherein said $R_fOR_f$— in said phosphine is

wherein z is zero or an integer having a value of 1 to 20.

10. The composition of claim 9 wherein said z is in the range of 1 to 4.

* * * * *